United States Patent [19]

Weitz

[11] Patent Number: 4,820,628

[45] Date of Patent: Apr. 11, 1989

[54] FETAL LUNG MATURITY TEST EMPLOYING LAMELLAR BODY SOLUBILIZATION

[75] Inventor: Stephen L. Weitz, Portland, Oreg.

[73] Assignee: State of Oregon, acting by and through the Oregon State Board of Higher Education, acting for and on behalf of the Oregon Health Sciences University, Portland, Oreg.

[21] Appl. No.: 868,452

[22] Filed: May 30, 1986

[51] Int. Cl.⁴ .............................................. C12Q 1/00
[52] U.S. Cl. .......................................... 435/4; 436/2; 436/34; 436/71; 436/164; 436/172
[58] Field of Search ..................... 435/4; 436/907, 909, 436/825, 829, 164, 172, 2, 34, 71

[56] References Cited

PUBLICATIONS

Oulton, "The Role of Centrifugation . . . in Amniotic Fluid", Am. J. Obstet. Gynecol., Oct. 1, 1979, pp. 337–343.
Oulton et al., "Assessment of Fetal Pulmonary Maturity . . . Lamellar Bodies", Am. J. Obstet. Gynecol. 03/15/82, pp. 684–691.
Oulton et al., "Developmental Study . . . From Human Amniotic Fluid", Pediatr. Res. 14: 722–728 (1980).
CRC Critical Reviews in Clinical Laboratory Sciences, vol. 16, Issue 2, Jan. 1982, pp. 85–157.
Tsai et al., "Absorbance of Amniotic Fluid . . . Tests for Disaturated Phosphatidylcholine and Phosphatidylglycerol", Am. J. Obstet. Gynecol., Aug. 15, 1983, pp. 963–966.
Weitz, et al., Clin. Chem., vol. 31, No. 6, (1985), p. 951.

*Primary Examiner*—Robert J. Warden
*Assistant Examiner*—Stephen C. Wieder
*Attorney, Agent, or Firm*—Millen & White

[57] ABSTRACT

The lamellar body solubilization test (LBST) is a rapid and simple indicator of fetal lung maturity. The amniotic fluid contains lamellar bodies, the presence of which can be correlated to maturation of lung tissue. The test is conducted by measuring a difference in an optical property (turbidity, light scatter, innate or added fluorescence) of a sample of amniotic fluid or other physical property affected by the presence of particulate bodies suspended in a liquid, either 1) kinetically (rate method) or 2) as an end point method (pre- and post-), due to the unravelling or solubilization of the lamellar bodies caused by subjecting the sample to a physical or chemical agent, e.g., detergent or heat. The change in that property either rate of change or delta, by the destruction of the lamellar body structure provides an accurate indication of the concentration and size of the lamellar bodies in the sample of amniotic fluid, which in turn provides a good indication of fetal lung maturity.

14 Claims, 6 Drawing Sheets

O.D. 650 vs. DELTA O.D. 650

DUE TO LAMELLAR BODY LIGHT SCATTER

| L/S | O.D. 650 | DELTA O.D. |
|---|---|---|
| 4.3 | 0.60 | 0.22 |
| 1.8 | 0.33 | 0.13 |
| 1.1 | 0.16 | 0.08 |

FIG. 6

FETAL LUNG MATURITY TEST EMPLOYING LAMELLAR BODY SOLUBILIZATION

BACKGROUND OF THE INVENTION

1. Field of the Invention

This invention relates to a novel fetal lung maturity test employing lamellar body solubilization and kits suitable for practicing the method of this invention.

Hyaline membrane disease is caused in part by inadequate lung cell synthesis of lamellar bodies (which contain surface-tension lowering material, surfactant). The neonatal hyaline membrane disease represents a major cause of perinatal mortality. It is therefore desirable to have a simple and rapid test which would permit a determination of lung maturity by determining lamellar body presence in amniotic fluid, the results of which would provide an indication of the neonatal pulmonary maturity. Desirably, the test should be simple, rapid and provides results that are easy to interpret.

2. Description of Prior Art

Several distinct methods exist for the assessment of fetal lung maturity. See Brown L. Duck-Chong C., "Methods of Evaluating Fetal Lung Maturity", *CRC Critical Rev. in Clin. Lab. Sci.* 16/2, 85-159 (1982).

The chromatographic measurement of phospholipid surfactants is time consuming, technically demanding, and fairly expensive. The "bubble" or foam stability index (U.S. Pat. No. 4,233,032) has potential for human error during the addition of the sample and human subjectivity in deciding a positive end point, i.e., what is a "stable foam". The "Amniostat" (U.S. Pat. Nos. 4,388,412 and 4,459,362), an immunological agglutination test suffers from the same drawbacks as the foam stability index. The $OD_{650}$ test, M. Y. Tsai et al., *Am. J. Obstet. Gynecol.*, 146:963, 1983, has the potential for nonspecific absorbance from nonsurfactant components of amniotic fluid. However, the result is less subject to human interpretation as compared with bubble and agglutination tests because it is read on a spectrophotometer.

From 1979 to 1982 Dr. Oulton published a series of articles demonstrating that amniotic fluid surfactant is present in globular-like structures which showed good correlation with fetal lung function. M. Oulton, *Am. J. Obstet. Gynecol.*, 135:337, 1979; M. Oulton et al, *Pediatr. Res.*, 14:722, 1980; and M. Oulton et al, Am. J. Obstet. Gynecol., 142:684, 1982. Dr. Oulton also characterized their content and development during gestational time. These data provide a sound theoretical basis for the concept of determining fetal lung maturity via the measurement of lamellar bodies.

Beginning in 1976 and more recently in 1983, Tsai et al, supra., the turbidity of amniotic fluid was used as an indicator of fetal lung maturity. The increasing turbidity during later stages of development is due to many factors, some of which include absorbance by small molecules, absorbance by large molecular structures and light scatter by macromolecular aggregates, including but not limited to lamellar bodies, and light scatter due to cells. Such nonspecificity, not to mention any due to contamination by other biological material, has caused mixed reviews among the clinical chemistry community.

One version of the subject invention has been described partially in the literature S. L. Weitz and J. R. Swanson, *Clin. Chem.*, 31:951, June, 1985; and additional abstract data presented at the annual meeting of the American Association for Clinical Chemistry, Atlanta, Ga. July 21-26, 1985.

OBJECTS OF THE INVENTION

It is an object of the invention to provide a novel method for determining fetal and neonatal lung maturity.

It is another object to provide such a method which is simple, rapid and provides results which are easy to interpret.

It is a further object to provide a kit comprising means for practicing the method of this invention.

Upon further study of the specification and appended claims, further objects and advantages of this invention will become apparent to those skilled in the art.

SUMMARY OF THE INVENTION

In a method aspect, this invention relates to a method for assaying fetal or neonatal lung maturity which comprises the step of measuring the change or rate of change in at least one physical property which is affected by the concentration of particulate bodies which are suspended in a liquid originating from a defined amount of the mother's amniotic fluid, which change is induced by destroying, either partially or totally, the lamellar body structure of the lamellar bodies in that liquid.

Such a method can be practiced by the steps of (a) measuring at least one physical property of a defined amount of the mother's amniotic fluid which is influenced by the presence of particulate suspended matter therein; (b) destroying the lamellar body structure of the lamellar bodies in that amniotic fluid; and (c) measuring the change in that physical property of the amniotic fluid resulting from such destruction of the lamellar body structure.

In a kit aspect, this invention relates to a kit for practicing the method of this invention comprising means permitting the measurement of the aforesaid property of a defined amount of amniotic fluid and a unit dosage amount of an agent capable of destroying the lamellar body structure of lamellar bodies in that defined amount of amniotic fluid.

DETAILED DESCRIPTION

This invention facilitates the detection of the potential for hyaline membrane disease (HMD) in a simple reliable manner by subjecting a defined amount of amniotic fluid to a physical agent capable of unravelling or solubilizing lamellar bodies and then measuring a change in optical properties resulting from the destruction of lamellar body structure.

Basically, the invention involves (a) the determination of a physical property, such as an optical property (i.e. absorbance) or number of particles (i.e. Coulter Counter), of a defined sample of amniotic fluid or a liquid derived therefrom, e.g., a physiological saline solution of the sample, which is affected by the concentration of lamellar bodies therein; (b) destroying the physical structure of the lamellar bodies in the sample; and (c) thereafter again determining the same property of the defined sample, the difference in the values obtained in steps (a) and (c) and/or the rate of change in those values correlating accurately with the concentration of lamellar bodies in the sample of amniotic fluid. The correlation between lamellar body content in amniotic fluid and fetal lung maturity is well known in the prior art. See, e.g., Oulton et al, *Rediatr. Res.*, 14722-728 (1981) and ibid., *Am. J. Obstet. Gynecol.*, 142:684, 1982; Tsai et al, *Am. J. Obstet. Gynecol.*, 146:963-966 (1983).

A wide variety of methods differing only in details may be employed in practicing this invention. Many different devices may be used for measuring a physical property of a sample of amniotic fluid which is affected by the amount of suspended particulate bodies therein. Such devices include spectrophotometers (flow through, test tube, cuvette, manual, part of an automated instrument, etc.), turbidometers, nephelometers, fluorometers, conductivity particle counters, and particle sorters.

The physical property which is measured preferably includes at least one member of the group consisting of absorbance, turbidity, light scatter, innate fluorescence and added fluorescence.

The term "destroyed" as used herein means, the structure of the lamellar bodies is altered sufficiently that the physical (optical) property affected by the lamellar bodies is significantly affected ordinarily, their structure is disrupted enough to at least partially solubilize the lamellar bodies. Physical agents that solubilize lamellar bodies which may be employed include, for example, heat, microwave energy, ultrasonic waves and chemical agents, including surfactants, e.g., detergents, and enzymes. These agents may be associated with the optical device or may be a separate item.

The method of this invention has been practiced by measuring $OD_{650}$ or $OD_{340}$ employing three currently used clinical chemistry instruments. All three instruments are mentioned in the paper presented by Weitz et al, supra., and include the Du Pont ACA II and V (using $OD_{340}$) as well as the Gilford Stasar III spectrophotometer (using $OD_{340}$ and $_{650}$). That paper contains information on analytical correlations with the L/S ratio which is currently the state-of-the-art standard in fetal lung maturity testing and also shows that the original concept (correlation with lipase activity) was false and that, in fact, detergent was responsible for the measured changes recorded by the instruments.

Distinct proof that lamellar bodies are solubilized by detergent was obtained by actually counting and sizing individual lamellar bodies using a fluorescence activated cell sorter. Unpublished data of S. Weitz, T. Bakke and J. R. Swanson, which are a collection of graphical results from a patient sample that was treated in 2 different ways (a control and the same sample plus detergent (triton x-100)) and measured at 2 different times each. The y and x axis show measurements of particle size and density, respectively. It can be seen from the data that the detergent has a dramatic effect on particle number and size. The size of the particles measured is really a measure of the light scattered by each individual lamellar body as it passes through the instrument. Thus, this experiment is direct proof of the assertions made previously in the papers of Weitz and Swanson. For information on the relationship of particle size to light scatter, see *Physical Biochemistry* by Kensal E. van Holde, Prentice-Hall, 1971.

The use of standards or control material for such a test would be desirable. Several possible ways of making such material exists. Synthetic lipid or phospholipid vesicles are useful because they are sensitive to the presence of detergent and their manufacture and stability are well described in the literature. Alternatively, animal or human amniotic fluid containing actual lamellar bodies can be used. Procurement of such fluid for pooling and packaging can easily be had from cesarean section pregnancies, which occur at a rate of 15-20% of all deliveries at major university hospitals. Such fluid is preferred because it would most closely resemble the patient samples to be measured.

We have found that the Dupont ACA lipase (LIP) method, which is an adaptation of the turbidometric method first described by Vogel and Zieve, *Clin. Chem.*, 9 (1963) 168-181, correlates with fetal lung maturity as determined by the L/S ratio when amniotic fluid is substituted for blood serum. Amniotic fluid lipase activity was not detectable with two other lipase methods. Rather than measuring lipase hydrolysis of triolein, the ACA LIP method may be recording the rate of turbidity clearing due to the detergent induced solubilization of the lamellar bodies present in more mature amniotic fluid. Such a rate determination might have inherent advantages over the established O.D. 650 and "bubble" methods. With modification of ingredients and timing, Dupont may be able to further optimize the test for use as an inexpensive and rapid screen for clearly mature and immature samples that would not require further time-consuming assessment.

Pulmonary lung surfactant, composed primarily of phospholipids, decreases the tendency for atelectasis which is a primary cause of respiratory distress syndrome in preterm infants. Several papers, viz., Vogel WC and Zieve L, supra; Heath MF and Jacobson W, *B.B. Acta*, 441 (1976) 443-452; and Herbert WNP, Johnston JM, MacDonald PC, and Jimenez JM, *Am. J. Obstet. Gynecol.*, 132 (1978) 373-379; have reported on the presence of phospholipid metabolizing enzymes in lamellar bodies of amniotic fluid. The reported enzyme activities were in the range of nanomoles per hour per milligram of protein. The present study was designed to examine amniotic fluid for the presence of relatively high levels of serum-like lipase activity using the insensitive (as compared with the radiotracer methods used above) du Pont ACA lipase (LIP) method. Activity was found and seemed to correlate with our in-house fetal lung maturity profile. However, two other lipase methods, fluorometric and turbidometric, detected no correlating lipase activity. The data and an explanation for the greater emulsion clearing observed with more mature samples using the ACA LIP method are presented below.

In the examples hereinafter, the method of this invention is practiced by measuring the $OD_{650}$ or $OD_{340}$ of the amniotic fluid before and after the lamellar bodies therein are solubilized and correlating either the $OD_{650}$ or $OD_{340}$ (end point method) or the rate of change in $OD_{650}$ or $OD_{340}$ (rate method) thus obtained in amniotic fluid of known lamellar body content.

Alternatively or additionally, another physical property of a liquid which is affected by the concentration of particulate matter suspended therein may be measured either to further increase the accuracy of the results or to adapt the method to the available equipment. For example, the Coulter method of particle counting and sizing may be used. The method is based on the detection and measurement of changes in electrical resistance produced by a particle, suspended in a conductive liquid, traversing a small aperature. This particle counter is commercially available from Coulter Electronics, Inc. A laser cell or particle sorter may also be used to quantitate the lamellar bodies before and after their destruction.

The exact nature of the kit aspect of tis invention will depend on the physical property of the amniotic fluid which is measured and the agent employed to solubilize the lamellar bodies in the amniotic fluid. It thus can be as (when a form of energy, e.g., heat, ultrasonic or microwave, is used as solubilizing agent) simple as a container for the amniotic fluid which permits measurement of the selected physical property of a defined volume (or cross-section) of amniotic fluid which is adapted to fit into the instrument employed to measure the selected volume plus a chart which correlates the range of values which will be obtained from such measurements to the possible range of lamellar body content or more preferably, to fetal lung maturity or additionally (when a chemical agent is employed as solubilizing agent) a unit dosage amount of a chemical solubilizing agent for the lamellar bodies in the defined amount of amniotic fluid.

Without further elaboration, it is believed that one skilled in the art can, using the preceding description, utilize the present invention to its fullest extent. The following preferred specific embodiments are, therefore, to be construed as merely illustrative, and not limitative the remainder of the disclosure in any way whatsoever.

In the preceding text and the following examples, temperatures are set forth uncorrected in degrees Celsius and all parts and percentages are by weight; unless otherwise indicated.

EXAMPLES

Materials and Methods

An ACA II and an ACA V (du Pont, ACA Division, Wilmington, Del. 19898), a Stasar II spectrophotometer (Gilford Instrument Laboratories, Oberlin, Ohio 44074), and a Photon immunoassay analyzer (Hybritech Inc., San Diego, Calif. 92121) were each used for different types of lipase assays.

Reagents

The Fetal-Tek borderline and mature control fluids were obtained from Helena Laboratories (Beaumont, Tex. 77704). The phosphatidyl glycerol, lecithin, and sphingomyelin standards were obtained from Sigma (St. Louis, Mo. 63178). Normal and abnormal control sera (for lipase determinations) were obtained from Ortho Diagnostics Systems (Raritan, N.J. 08869). ACA Lipase calibrators were obtained from du Pont Wilmington, Del. 19898).

Procedures

Amniotic fluid was centrifuged for 5 minutes at 1000 x g to remove cellular material. Freshly centrifuged fluid was then extracted with methanol:chloroform (1:1) and the phospholipids were separated by 2-D TLC. The dried plate was sprayed with a solution of cupric acetate and the phosphoric acid each at 8% w/v. Quantitation was by densitometry after baking the TLC plate at 85 degrees C.

The bubble test is the method of Clements et al, *N. Eng. J. Med.*, 284 (1972) 1077.

In the first experiment, a Du Pont ACA II was set to inject a 200 $\mu$l aliquat of centrifuged amniotic fluid (either fresh or previously frozen) into a LIP pack. All parameters were identical with the normal serum lipase assay. In the second experiment, channel B of the Lipase assay on a Du Pont ACA V was set to inject a 500 $\mu$l aliquat of centrifuged amniotic fluid (only fresh, no frozen) into a LIP pack. The total volume remained the same by reducing the diluent volume by 300 $\mu$l.

Two alternative lipase methods were used as a correlation with the first study. The first was the turbidometric method of Shihabi and Bishop, *Clin. Chem.*, 17 (1971) 1150–1153, which was run on the Gilford Stasar III. The second was a fluorometric lipase or esterase method, Fleisher M. and Schwartz M., *Clin. Chem.*, 17 (1971) 417–422; and Guibault GG and Kramer DN, *Anal. Chem.*, 36 (1964(409), which used fluorescien dilaurate as substrate. The photon immunoassay analyzer was used in the fluoroscence mode to measure the release of fluoroescien by action of a lipase or esterase.

BRIEF DESCRIPTION OF THE DRAWINGS

Various other objects, features and attendant advantages of the present invention will be more fully appreciated as the same becomes better understood when considered in connection with the accompanying drawings wherein:

FIG. 6 shows the correlation between the L/S method, the O.D. 650 method, and the Delta O.D. 650 method which is similar to what is occuring in the Du Pont amniotic fluid "lipase" method. (The Delta 0.D. 650 method is the difference in optical density of 650 nm light, measured before and after the addition of Triton X-100.)

Figure 1:
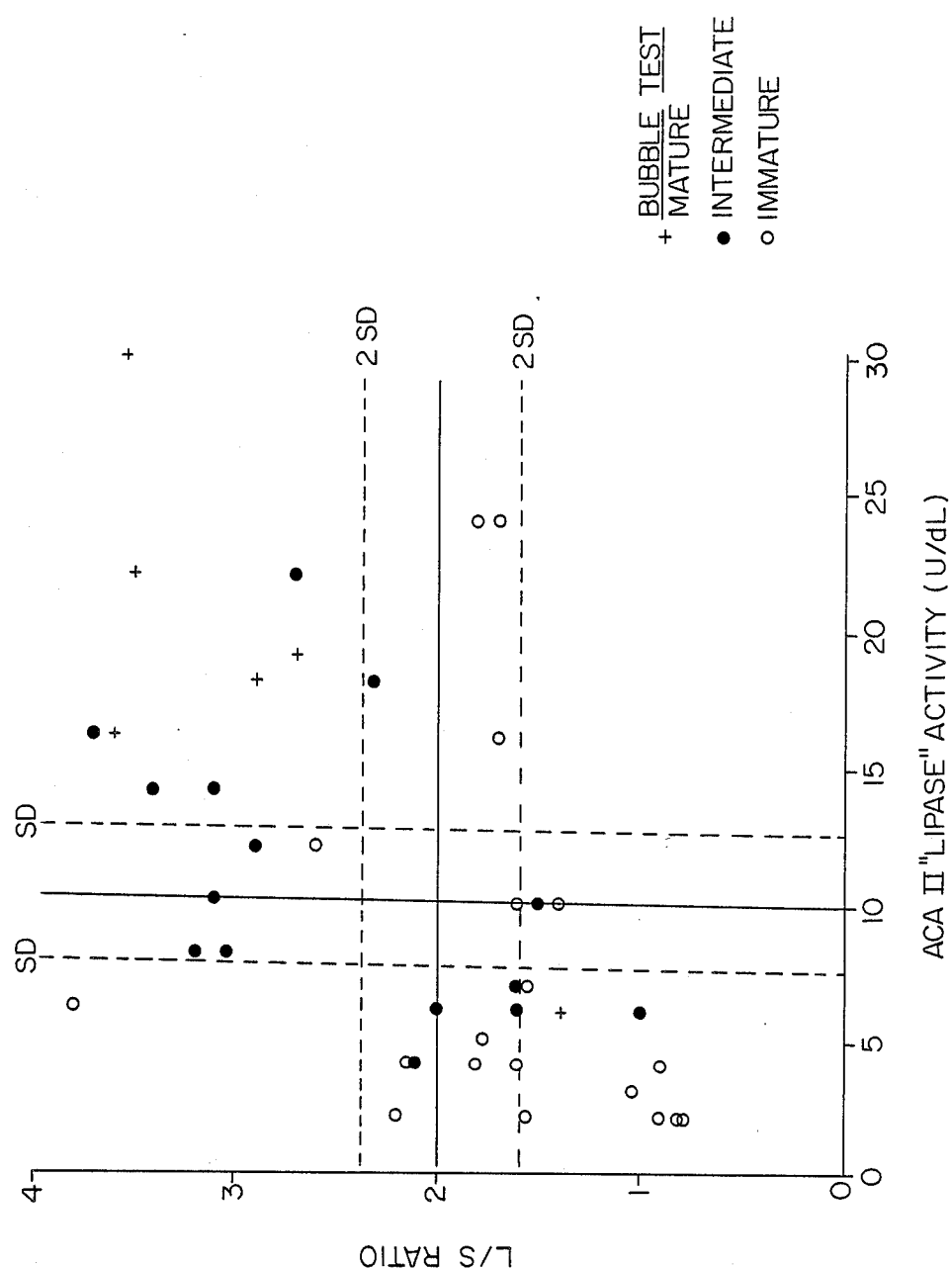
FIG. 1 is a scatter plot of the L/S ratio vs "lipase" activity as determined with a 200 $\mu$l aliquat of amniotic fluid using the ACA II, the horizontal line at L/S - 2.2. showing the mature cutoff value used in the laboratory.
Figure 2:
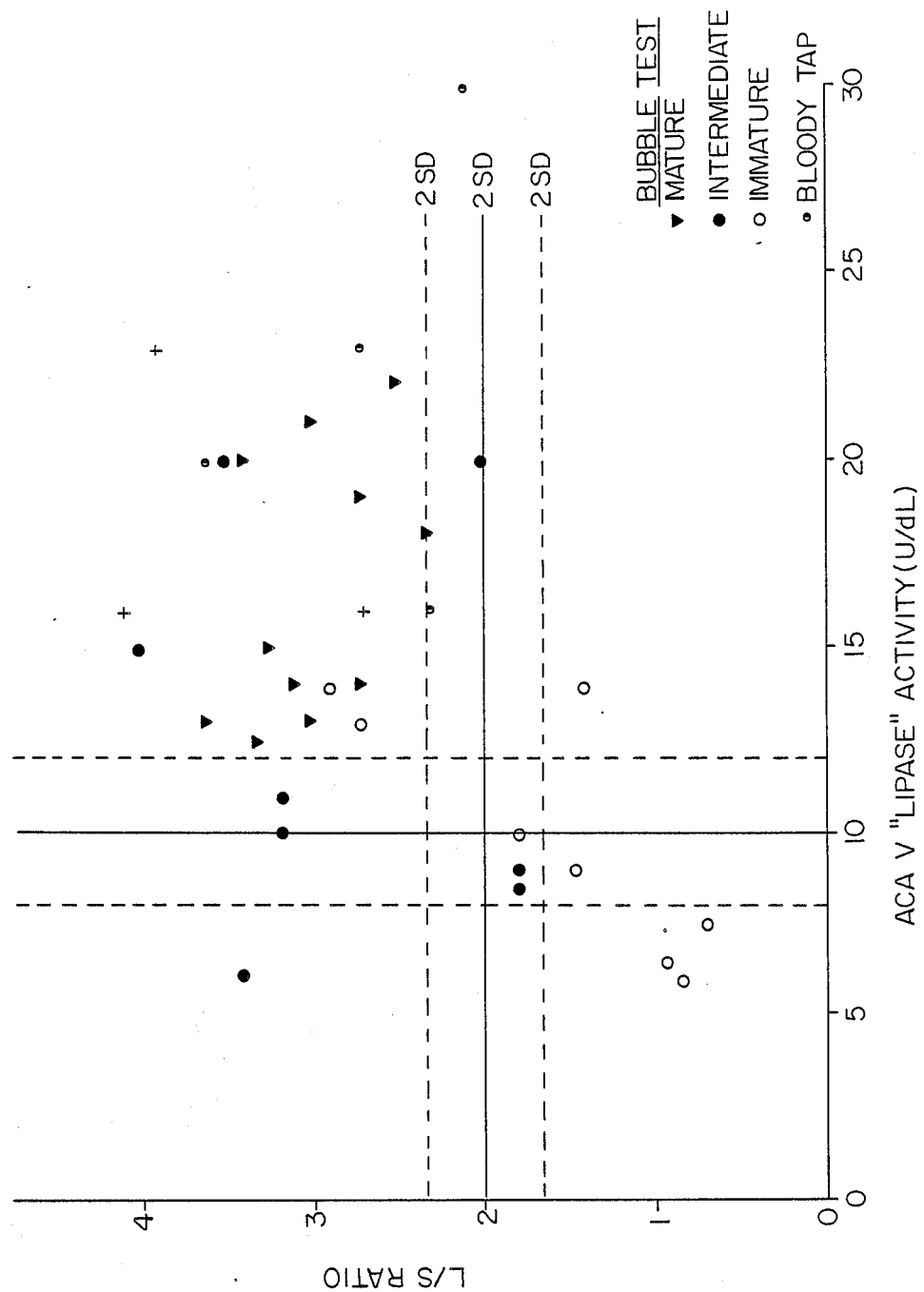
FIG. 2 is a scatter plot of the L/S ratio vs "lipase" activity as determined with a 500 $\mu$l aliquat of amniotic fluid using the ACA V, the horizontal line at L/S - 2.2. showing the mature cutoff value used in this laboratory and the lines above and below being equal to two standard deviations of the L/S method as determined from control samples at a ratio of 2.0.
Figure 3:
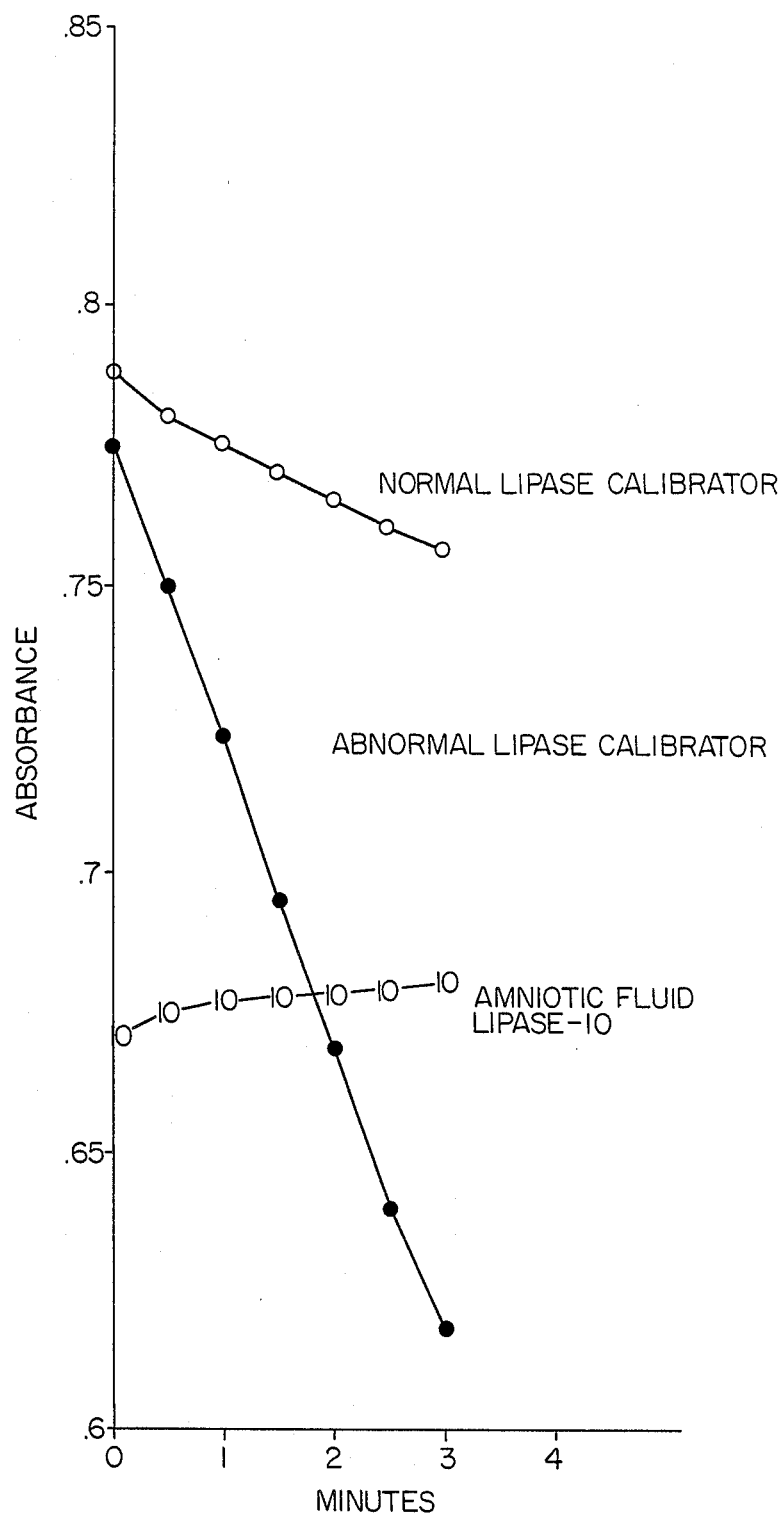
FIG. 3 is a plot of lipase control activity and patient samples using the turbidity clearing method.
Figure 4:
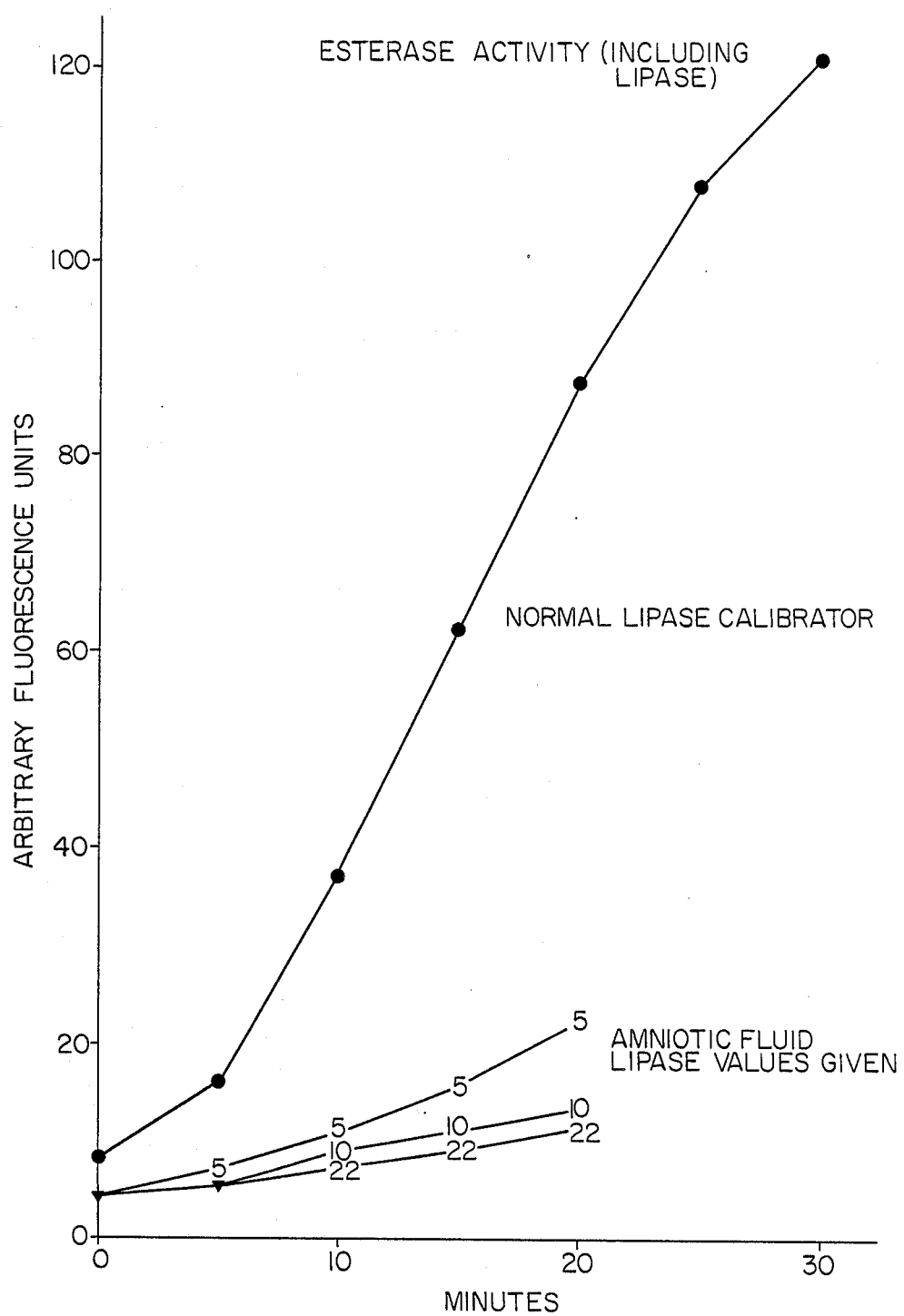
FIG. 4 is a plot of the same lipase control and patient samples; both methods showing that the "lipase" activity in the Du Pont method is due to some other kind of activity.
Figure 5:
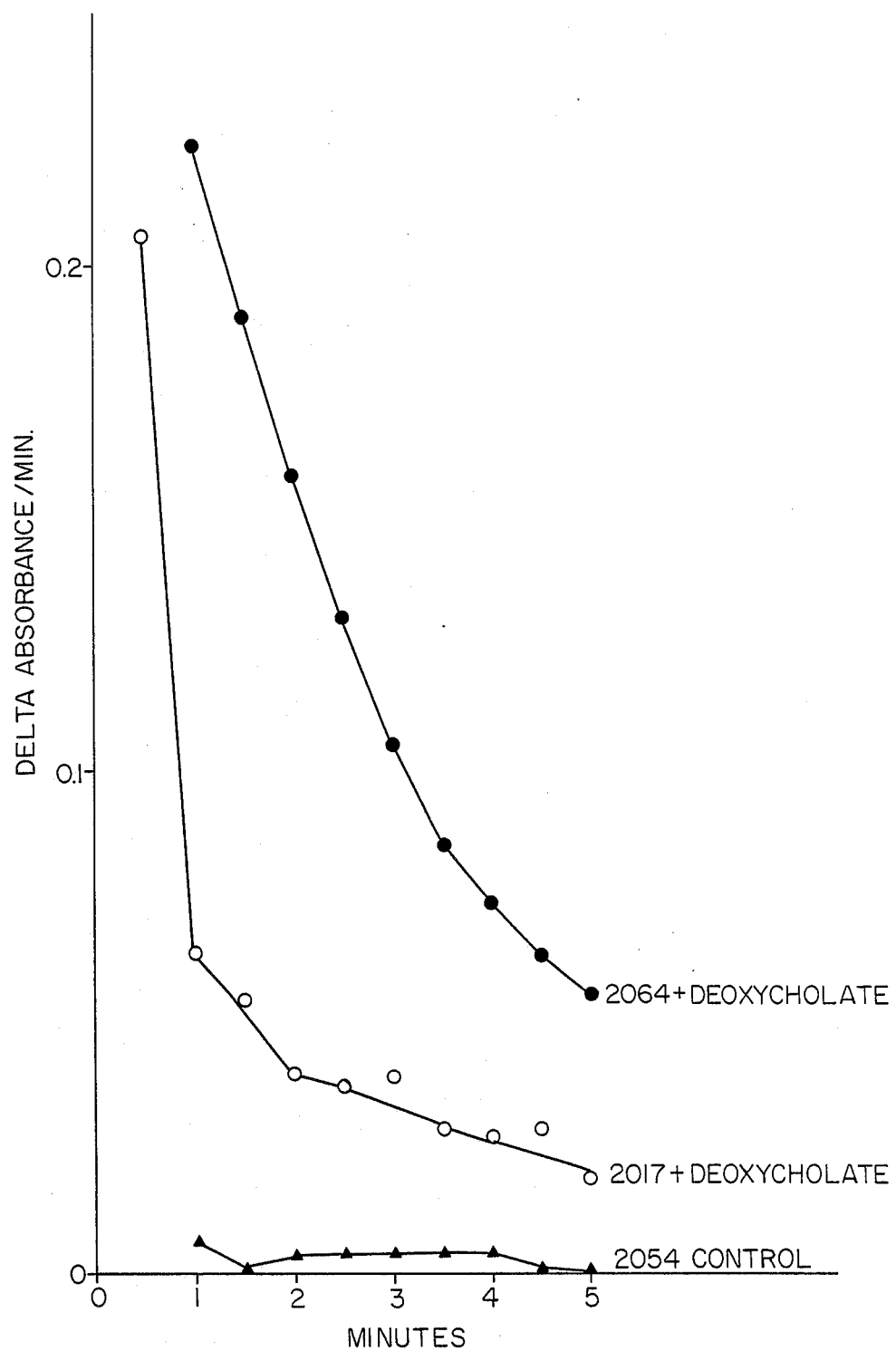
FIG. 5 shows kinetically the clearing due to the addition of detergent to a patient sample.

The method of this invention can employ the Du Pont ACA lipase (LIP) method (a turbidometric assay for detection of serum lipases). When amniotic fluid is substituted for serum in that method, it correlates with the Lecithin/Sphingomyelin (L/S) ratio. However, similar amniotic fluid lipase activity was not detectable with two other lipase methods. Rather than measuring lipase hydrolysis of triolein, the LIP method senses the rate of turbidity clearing due to detergent induced solubilization of the lamellar bodies present in more mature amniotic fluid. Analytically important data for 39 patient samples are presented below (bubble test, *N. Eng. J. Med.*, 284, 1077, 1972):

| Parameter | L/S | Bubble | Lipase (ACA 3) |
| --- | --- | --- | --- |
| Sample Size | 2 ml | 2 ml | 0.2 ml |
| C.V. (N) | 10–16% (19) | — | 26% (5) |
| Immature Range | <2 | −Ring | <8 U/dL |
| Ambiguous Range | 1.7–2.3 | +1 Tube | 8–12 U/dL |
| Mature Range | >2 | +2 Tubes | >12 U/dL |
| Agreement With | Immature | 87% | 94% |

| Parameter | L/S | Bubble | Lipase (ACA 3) |
|---|---|---|---|
| L/S Method | Mature | 83% | 100% |
| % Samples in Ambiguous Range | 18% | 41% | 25% |

In the above studies the LBST was less ambiguous and had a greater degree of accuracy than the often used bubble test. The LBST thus is quick, economical, and from the data we obtained diagnostically more useful than the bubble test as a rapid screen for clearly mature and immature samples which would not require further time consuming assessment (i.e., L/S ratio).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for assaying fetal or neonatal lung maturity which comprises the steps of (a) measuring at least one physical property of a fluid containing the lamellar bodies present in a defined amount of a mother's amniotic fluid, which property is one which is affected by the concentration of particulate bodies which are suspended in a liquid; (b) destroying partially or totally the lamellar body structure of the lamellar bodies in that liquid; and (c) measuring the change or rate of change in that physical property of the liquid resulting from such partial or total destruction of the lamellar body structure said change or rate of change being an indication of said lung maturity.

2. A method according to claim 1, wherein the lamellar body structure is destroyed by a solubilizing reagent.

3. A method according to claim 2, wherein the solubilizing agent is an enzyme.

4. A method according to claim 2, wherein the solubilizing agent is a surfactant.

5. A method according to claim 4, wherein the surfactant is an ionic or nonionic detergent.

6. A method according to claim 1, wherein the surfactant is an organic solvent.

7. A method according to claim 1, wherein the lamellar body structure is destroyed with ultrasonic energy.

8. A method according to claim 1, wherein the lamellar body structure is destroyed with heat.

9. A method according to claim 1, wherein the physical property of the amniotic fluid which is measured includes at least one member of the group consisting of absorbance, turbidity, light scatter, innate fluorescence and added fluorescence.

10. A method according to claim 1, wherein the physical property of the amniotic fluid which is measured is absorbance.

11. A method according to claim 1, wherein the absorbance wavelength of light is in the range 190 to 700 nanometers.

12. A method according to claim 1, wherein the change in the physical property is measured.

13. A method according to claim 1, wherein the rate of change in the physical property is measured.

14. A method according to claim 1, wherein the lamellar body structure is destroyed by a solubilizing surfactant; and wherein the change in optical density at 340 nm is measured.

* * * * *